United States Patent [19]

McGhee

[11] 4,049,997
[45] Sept. 20, 1977

[54] DRIVE FOR DYNAMIC MECHANICAL SYSTEM

[75] Inventor: John D. McGhee, Plymouth Meeting, Pa.

[73] Assignee: E. I. Du Pont de Nemours and Company, Wilmington, Del.

[21] Appl. No.: 662,270

[22] Filed: Feb. 27, 1976

[51] Int. Cl.² .......................................... H02K 33/00
[52] U.S. Cl. .................................... 318/128; 73/71.6; 310/27; 318/132
[58] Field of Search .............................. 310/27, 131; 318/127–132, 133, 139; 73/71.6; 307/252 UA

[56] References Cited

U.S. PATENT DOCUMENTS

| 2,935,672 | 5/1960 | Ross | 318/132 X |
|---|---|---|---|
| 3,486,094 | 12/1969 | Zane | 318/128 |
| 3,504,250 | 3/1970 | Stevens, Jr. et al. | 318/128 |
| 3,787,715 | 1/1974 | Eaton, Jr. | 318/130 |
| 3,872,333 | 3/1975 | Imbert et al. | 310/27 X |

*Primary Examiner*—Donovan F. Duggan

[57] ABSTRACT

A dynamic mechanical system is driven at its resonant frequency by a drive system which maintains the vibrational amplitude of the system constant. A displacement transducer senses the mechanical displacement of the system and provides a displacement signal which is used to generate a control signal related to the energy necessary to maintain the mechanical system in resonance. The zero crossover points of the displacement signal are shifted in-phase 90° and used to selectively switch the control signal to provide an in-phase drive signal for the system. An offset correction system senses any asymmetry present in the displacement signal and adjusts the drive signal to compensate for such asymmetry so that the mechanical system operates about a zero point of the displacement transducer.

7 Claims, 2 Drawing Figures

DRIVE FOR DYNAMIC MECHANICAL SYSTEM

BACKGROUND OF THE INVENTION

For many materials, including practically every man-made synthetic material, the mechanical behavior during processing as well as end product conditions is an important parameter that must be tightly specified and controlled. During the initial phases in the development of a new polymer or process, an understanding of the relationship between chemical structure and the physical properties of the process is of vital concern. Later on, in the process and quality control stages, factors such as mechanical strength, dimensional and thermal stability, and impact resistance are of utmost importance.

Virtually all synthetic materials in existence are viscoelastic, i.e., their behavior under mechanical stress lies somewhere between that of a pure viscous liquid and that of a perfectly elastic spring. Few materials behave like a perfect spring or a pure liquid. Rather, the mechanical behavior of these materials is generally time and/or temperature dependent and has led to such tests as creep, stress relaxation, tear, impact resistance, etc. One of the more important properties of materials sought is the materials' behavior under dynamic conditions. To explore this, a material's response to a cyclical stress as a function of temperature, time or frequency is determined. If a sample of a viscoelastic solid, for example is deformed and then released, a portion of the stored deformation energy will be returned at a rate which is a fundamental property of the material. That is, the sample goes into damped oscillation. A portion of the deformation energy is dissipated in other forms. The greater the dissipation, the faster the oscillation dies away. If the dissipated energy is restored the sample will vibrate at its natural (resonant) frequency. The resonant frequency is related to the modulus (stiffness) of the sample. Energy dissipation relates to such properties as impact resistance, brittleness, noise abatement, etc.

Because of their viscoelastic nature, the stress and strain in viscoelastic materials are not in phase, and, in fact, exhibit hysteresis. If a plot is made of this relationship, the area enclosed by the plot corresponds to the energy dissipated during each cycle of deformation of the material. In order to accurately describe this phenomenon, a complex modulus $E = E' + jE''$ is often used to characterize the material where E is Young's modulus, $E'$ is the real part and $E''$ is the imaginary part. The real part $E'$ of the modulus corresponds to the amount of energy that is stored in the strain and can be related to the spring constant, the complex part $E''$ corresponds to the energy dissipation or damping and can be related to the damping coefficient used in second order differential equations to define vibrating systems.

Many mechanical analyzers have been developed for testing and ascertaining such properties as the modulus and elasticity of materials and the variations of these properties as a function of both time and temperature. Among these systems are those described for example in U.S. Pat.Nos. 3,501,952 issued Mar. 24, 1970 to Gergens et al; 3,508,437 issued Apr. 27, 1970 to Van Beek; and, 3,751,977 issued Aug. 14, 1973 to Schilling. All of these systems place the sample under test into vibration or oscillation utilizing mechanical systems. These mechanical systems vibrate at a resonant frequency determined primarily by the sample. A drive transducer is used to maintain the system in oscillation, a displacement transducer is used to sense the displacement of the mechanical system, and a drive amplifier is used to energize the drive transducer sufficiently to maintain the system oscillating at resonance and at a constant amplitude.

Among the problems encountered using these prior systems have been that of balancing the system to oscillate symmetrically about a zero point, the difficulty of obtaining a sample signal related to the power loss within the system and hence to the complex or loss modulus of the sample, the difficulty of operating the systems over wide dynamic ranges of frequencies and yet maintaining system balance, and the difficulty of operating repeatedly and consistently at relatively low resonance frequencies approaching the order of one cycle per second.

Accordingly it is an object of this invention to obviate many of the disadvantages inherent in prior art drives for dynamic mechanical systems.

Another object of this invention is to provide an improved system for driving a dynamic mechanical system at its resonanct frequency.

SUMMARY OF THE INVENTION

This invention finds use in a system for driving a dynamic mechanical system at its resonant frequency. Typically such mechanical system, which may be used to ascertain various physical characteristics including the complex modulus of a sample, includes a displacement transducer for providing an alternating signal corresponding to the instantaneous displacement of the mechanical system, a drive transducer for imparting mechanical motion to the system, and drive means responsive to the displacement signal for actuating the drive transducer to maintain the mechanical system oscillating at its resonant frequency and at a constant amplitude. The invention provides an analog means for developing an analog signal related to the power required to maintain the amplitude of oscillations constant and switching means responsive to the zero crossover times of the alternating displacement signal for selectively actuating the drive transducer with the analog signal to maintain the resonant frequency.

In a particularly preferred embodiment, the switching means includes phase shift means for selectively actuating the drive transducer to operate in-phase with the mechanical system. Further an integrating means is responsive to the displacement signal for generating an offset signal related to any asymmetry of the displacement signal. This offset signal is added to the switched analog signal which drives the mechanical system in order to automatically zero the system with respect to the displacement transducer. This permits the system to accommodate broad frequency ranges, low as well as high. Further the phase shift means includes means for shaping the displacement signal into a rectangular waveform to provide a squared signal, a second integrator for integrating the squared signal, and amplifier means responsive to the integrated squared signal for providing a timing signal phase shifted from the 90° crossover times to actuate the drive means in-phase with the mechanical system. Finally a gain control integrator means is responsive to the displacement signal departing from a predetermined amplitude to adjust the amplitude of the analog signal in a sense to maintain said predetermined amplitude.

BRIEF DESCRIPTION OF THE DRAWINGS

Further advantages and features of this invention will become apparent upon consideration of the following description wherein.

DESCRIPTION OF THE PREFERRED EMBODIMENTS

Figure 1:
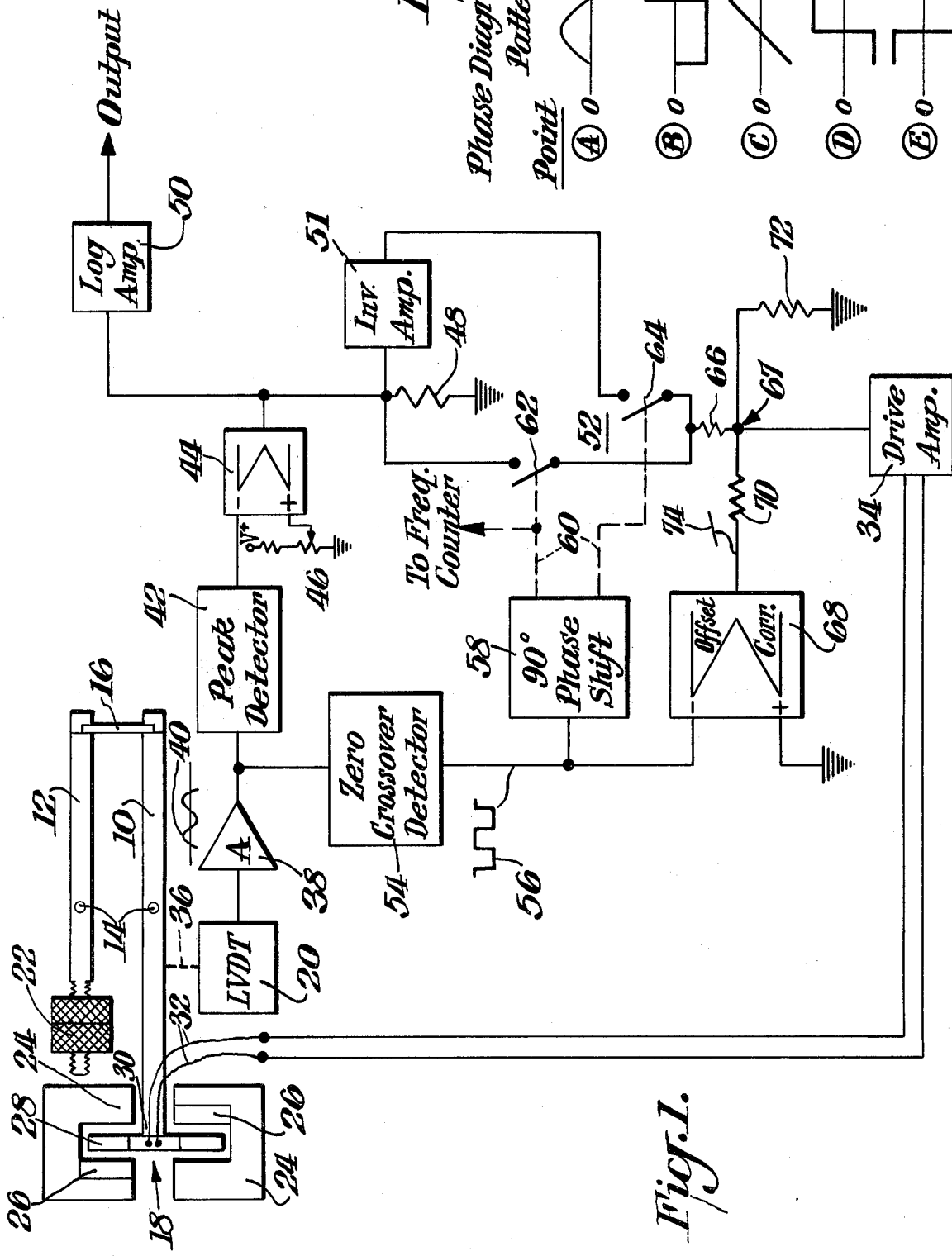
FIG. 1 is a block diagram of a drive system for a dynamic mechanical system constructed in accordance with this invention.

There is described in a copending application Ser. No. 662,269 filed Feb. 27, 1976 filed by Woo et al. and assigned to the same assignee as this application, a dynamic mechanical analyzer for testing materials. As is described by Woo et al., such analyzer may be used to measure the complex modulus and other physical properties of materials. This measurement is made by subjecting a sample of the material under test to a well defined mechanical oscillatory motion, preferably one in which the sample is placed under a shear stress. By measuring these physical properties of materials, information as to the polymer structure of the material can be ascertained. The Woo et al. analyzer, as depicted in FIG. 1, incorporates two parallel sample arms 10, 12 (a driving arm 10 and a driven arm 12) each pivotally mounted at their central portion by flexure pivots 14 having precisely known, low spring constants. A sample 16 is clamped between one end of each of the arms 10, 12 such that the only coupling between the arms is the sample. An electromechanical driver 18 is positioned at the opposite end of the driving arm 10 together with a displacement transducer 20. The remainder of the block diagram seen in FIG. 1 of the drawing constitutes a control arrangement for maintaining the inphase oscillation of the arms 10 and 12 at a constant amplitude and at the resonant frequency of the system as determined primarily by the complex modulus of the sample 16 and the spring constant of the flexure pivots 14, if flexure pivots are used. The driven arm 12 has a counter weight 22 which is used to balance the arm dynamically about its pivot 14.

Among the advantages of this system is that the displacement transducer 20 is remote from the sample 16; hence, when the sample is subjected to heating or cooling, the transducer stability is not affected.

In accordance with this invention, the electromechanical driver 18 is designed to provide a relatively linear drive. To accomplish this, a linear drive system is employed and incorporates a pair of U-shaped iron pole pieces 24, a permanent magnet such as a ferrite magnet 26 associated with each pole piece, and a pancake coil 28 disposed in the air gap provided by the pole pieces 24 and the magnets 26 The pancake coil 28 is a uniformly wound, flat coil secured to the driven end 30 of the driving arm 10. Lead wires 32 from the pancake coil are connected to a drive amplifier 34 which supplies the necessary current for causing the coil to move within the magnetic field (at right angles to the field) and thereby cause a vibratory or oscillatory motion of the driving arm 10 about the pivot 14, as will be described. The driven arm 12, coupled via the sample 16 to the driving arm also oscillates substantially in-phase with the driving arm, the frequency and amplitude of the oscillation being primarily determined by the complex modulus of the sample.

This mechanical motion of the arms 10 and 12 is sensed by a suitable displacement transducer 20 which may be any of those well known in the art. Preferably this transducer may be a linear voltage differential transformer of known type which is mechanically coupled as depicted by the dashed line 36 to one of the arms, in this case to the driving arm 10. As is known, a linear voltage differential transformer displacement transducer provides an output voltage signal which varies in amplitude and frequency in accordance with the movement of the arm 10 whose displacement is being sensed. This displacement signal is amplified by an amplifier 38 to provide an alternating waveform such as is depicted by the curve 40. The amplifier displacement signal 40 is passed to a peak detector 42 which provides a direct current output signal varying in amplitude in accordance with the peak amplitudes of the signal 40. This peak detected signal is coupled to the negative-going input of a gain control integrator 44 so that it may be compared with a predetermined reference level, such as is established by a potentiometer voltage divider 46, which is applied to the positive-going input of the same integrator. Thus the output of the integrator 44 will be a relatively constant voltage level or analog signal which is developed across an output resistor 48. By proper adjustment of the voltage divider 46, the analog signal developed across the output resistor 48 may be related to the power required in the system to maintain the amplitude of the mechanical vibrations or oscillations constant. Thus by time switching the analog signal and using the switched signal to drive the system, the amplitude of the oscillations of the arms is maintained constant. Also by amplifying it using any suitable type of logarithmic amplifier 50, the dynamic range of the output is enhanced. The analog signal developed across the output resistor 48 is coupled through a switching circuit 52 to the drive amplifier 34 which energizes the drive transducer 18 to maintain the mechanical system in oscillation.

The switching system 52 functions, as will be described, to maintain the signals applied to the drive amplifier 34 in-phase with the vibratory motion of the mechanical system. This is accomplished by a zero crossover detector 54 which is a high gain amplifier that shapes, due to its high gain, the signals into a rectangular waveform 56. Hereinafter such amplifiers will be referred to as squaring amplifiers. The vertical going components of the waveform 56 correspond in time to the zero crossover points of the displacement signal 40. This rectangular signal is sent through a 90° phase shifter 58 which may be of conventional design, to change the phase of this rectangular signal 56 such that the zero crossovers correspond in time to the peaks of the displacement signal 40. It is these phase shifted signals which are used to control the switching circuitry 52. This phase shift circuit 58 has outputs depicted by the dashed lines 60 which may be relays but preferably are analog switches 62 and 64 respectively. These analog switches may be of a known type such as integrated circuit chips NC 14016CP. To this end, the first switch 62 connects the analog voltage across the resistor 48 through resistor 66 to a summing point 67 which is the input of a drive amplifier 34. In like manner the voltage across the resistor 48 is coupled through an inverting amplifier 51 of conventional design, the second analog switch 64, and the summing resistor 66 to the summing point 67.

Finally, there is provided an offset correction circuit which receives the rectangular waveform 56 and automatically adjusts the drive voltage of the mechanical system. This offset correcting circuit may include an integrating circuit 68 in which case the rectangular waveform 56 is connected to the negative-going input of the integrator and the positive-going input is referenced to ground. The output of this integrator is thus a signal whose level varies in accordance with the asymmetry of the signal derived from the displacement transducer 20. This asymmetry may be due to asymmetrical placement of the transducer itself, asymmetrical vibration due to a misaligned drive system, or misalignment in mounting the sample 16. In any event, any asymmetry in the system as manifested in the displacement waveform will be corrected by this integrator 68 by changing the level of the voltage which is coupled through a summing resistor 70 to the summing point 67. The summing point 67 is connected through a resistor 72 to ground. The offset signal is a slowly varying DC level depicted by the waveform 74 and is combined with the switched voltages from analog signal developed across resistor 48 to control the operation of the drive transducer 18. The offset correction integrator 68 adjusts the displacement waveform 40 such that the crossover times are equally spaced; i.e., symmetrical in time. This has a particular advantage in that it permits the mechanical system to be operated at relatively low frequencies as well as at high frequencies without readjustment of the balance of the system. Such readjustment is automatic and operates through the drive transducer 18.

Figure 2:
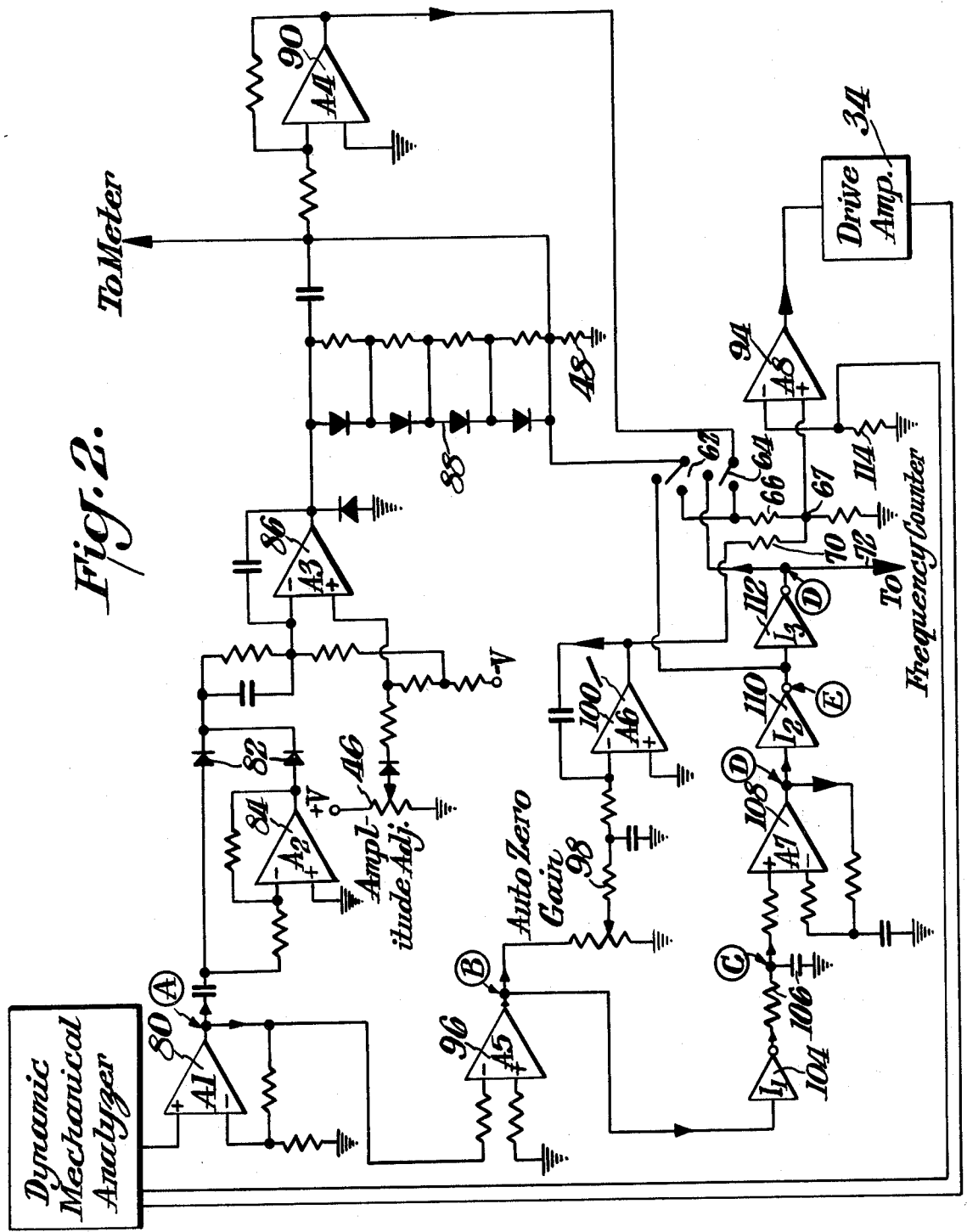
FIG. 2 is a schematic diagram of a portion of the drive system illustrated in FIG. 1; and, FIG. 3 is a series of waveforms depicting the operation of the circuit illustrated in FIG. 2.

The details of a preferred schematic implementation of the system of FIG. 1 will best be understood by reference to the schematic circuit of FIG. 2. The operation of the circuit will be described in connection with the waveforms of FIG. 3. As is seen in FIGS. 2 and 3, the input displacement signal from the displacement transducer 20 is amplified by a noninverting amplifier 80 and thereafter passed to a pair of parallel connected, peak detecting diodes 82. The signal from the amplifier 80, depicted by the waveform A of FIG. 3, is connected directly to one diode 82 and through an inverting amplifier 84 to the second diode 82, both diodes 82 being poled in the forward conducting direction, i.e., the cathodes of both diodes are connected to a common point. In turn the common point is connected to the negative-going terminal of an integrater 86. The positive-going terminal of the integrator 86 is connected to a source of reference potential as depicted by the adjustable potentiometer 46 connected as a voltage divider. The output of this integrator 86 thus provides an analog voltage level which is developed across a resistor 48 which varies as a function of the voltage needed to maintain the vibrational amplitude of the system at a constant level.

This may easily be understood by considering the fact that if the displacement signal increases in amplitude, the integrator will decrease its output voltage level thereby decreasing the amplitude of the signal applied to the drive amplifier 34. The converse is also true — if the amplitude or displacement signal decreases, the reference potential from the reference potentiometer 46 will cause the integrator to integrate upwardly, thereby increasing the magnitude of the drive signal.

The output of the integrator is connected through a diode-resistor ladder type network 88 which functions as a sensitivity adjusting network. With this network, large amplitude drive signals will require a larger change in amplitude to develop a voltage across the resistor 48 than do smaller amplitude drive signals as typically are required when operating with less stiff samples. The diode bridge network 88 comprises a plurality of serially connected diodes connected between the output of the integrator 86 and the summing resistor 48. Each of the diodes is paralleled by a resistor; each of the resistors also being in series between the output of the integrator 86 and the summing resistor 48. In this manner, large amplitude changes in amplitude drive signals which typically are required for stiffer samples, are immediately passed through the network. This occurs because more of the diodes are forward biased— hence small changes in the amplitude of the signal from the displacement transducer are more easily summed across the summing resistor 48. Conversely, with less stiff samples which typically require smaller amplitude driving signals, fewer of the diodes are conducting; hence, a much larger change in an amplitude displacement signal is required to overcome the forward bias of the diodes before there is a corresponding change in the drive signal.

The voltage developed across the summing resistor 48 is coupled through an inverting amplifier 90 to an analog switch 64 and directly through a second analog switch 62, through a resistor 66 to a summing point 67 having a summing resistor 72 connected to a ground. The summing point 67 is connected through a non-inverting amplifier 94 to drive the pancake coil 28 (FIG. 1). To provide the necessary timing for the switches as well as the offset signal, the amplified displacement signal, depicted by the waveform A of FIG. 3, is coupled to the inverting input of a zero crossover amplifier 96. The output of this amplifier 96 is a rectangular wave depicted by the waveform B of FIG. 3. This square wave signal is integrated in a conventional RC integrator 98 and thence passed to the negative-going terminal of an integrator 100 to provide a signal level whose amplitude changes in accordance with the asymmetry of the displacement signal. This offset signal is passed through a summing resistor 70 to the summing point 67 so that it may affect the drive signal applied to the pancake coil as was described previously.

The square wave B is also coupled to an inverter 104, whose output is connected to an RC integrator 106. The integrator output is connected to a further high gain amplifier 108. The integrated signal, which is depicted by the triangular waveform C, when applied to the amplifier 108 results in a 90° phase shift, as depicted by the waveform D. This time shifted signal represented by waveform D, coincides in time with sequential positive and negative going peaks of the displacement signal represented by the waveform A. Thus this waveform D may be used to control the switching times of the switches and hence provide in-phase driving signals for the transducer 18. The time shifted signal may be inverted by an invertor 110 to provide a signal, represented by the waveform E, which is complementary or drive waveform used to control the first analog switch 62. This inverted signal is again passed through an inverter 112 to provide a waveform inphase with the waveform D to control the second analog switch 64. The output of either of these inverters may be passed to a suitable frequency counter to provide a signal indicative of the modulus of the sample under test. The drive signal from the pancake coil may be fed back to the negative input of the amplifier 94 and summed across the resistor 114 such that the voltage across this resistor gives a feedback response representative of the signal called for.

This system thus described is seen to provide a relatively constant direct current output signal which is related to the loss modulus of the material under test. At the same time the system provides an output signal whose frequency is related to the modulus of the material. By relating the control signal to the actual displacement of the system an automatic means of adjusting for offsets, either of the displacement transducer or the system operation itself, is provided. Any offset manifested in the form of an asymmetrical waveform from the displacement transducer is immediately sensed and automatically corrected. Further, by sensing timing, the drive signal correlates directly with the displacement of the mechanical system and wide frequency ranges are permitted without having to readjust or recalibrate the system. The use of the linear drive made possible by the use of a pancake coil, the windings of which operate entirely within a magnetic field, averts errors that can occur due to drive non-linearity.

The several amplifiers and integrators used in the circuit of FIG. 2 are conventional and may for example be integrated circuit chips:

| Element | Chip |
|---|---|
| 80, 84, 90, 94, 96, 108 | LM308N or HA2645 |
| 86, 100 | LM308N |
| 104, 110, 112 | MC14049CP |

Drive amplifiers 34 may be a push-pull transistor amplifier of conventional design.

I claim:
1. In a system for driving a dynamic mechanical system at its resonant frequency, said mechanical system having a displacement transducer for providing an alternating signal corresponding to the instantaneous displacement of said mechanical system, a drive transducer for imparting mechanical motion to said system, and drive means responsive to said displacement signal for actuating said drive transducer to maintain said mechanical system oscillating at said resonant frequency and at a constant amplitude, the improvement wherein:
   said drive means includes analog means for developing an analog signal related in amplitude to the power required to maintain said amplitude constant,
   switching means responsive the the zero crossover times of said alternating displacement signal for selectively actuating said drive transducer with said analog signal to maintain said resonant frequency,
   said switching means includes inverting means for inverting the polarity of said analog signal, and
   additional switching means responsive to alternate pairs of successive peaks of said displacement signal and to said inverted analog signal for selectively actuating said drive transducer to drive said mechanical system in both senses.

2. In a system according to claim 1 the improvement wherein said switching means includes integrator means responsive to said displacement signal for generating an offset signal related to any asymmetry of said displacement signal, and
   adder means for adding said offset signal to said switched analog signal to adjust said system to remove said asymmetry.

3. In a system according to claim 2 the improvement wherein said switching means includes phase shift means for squaring said displacement signal,
   second integrator means for integrating said squared signal, and
   amplifier means responsive to said integrated squared signal for providing a timing signal phase shifted 90° from said zero crossover times to actuate said drive means in-phase with said mechanical system.

4. In a system according to claim 3 the improvement wherein said switching means includes gain control integrator means response to said displacement signal departing from a predetermined amplitude for adjusting said analog signal in a sense to maintain said predetermined amplitude.

5. In a system according to claim 4 the improvement wherein said switching means includes peak detector means responsive to said displacement signal for generating a control level,
   a source of a reference level,
   said gain control integrator means operating in response to said levels to adjust said analog signal.

6. In a system for driving a dynamic mechanical system at its resonant frequency, said mechanical system having a displacement transducer for providing an alternating signal corresponding to the instantaneous displacement of said mechanical system, a drive transducer for imparting mechanical motion to said system, and drive means responsive to said displacement signal for actuating said drive transducer to maintain said mechanical system oscillating at said resonant frequency and at a constant amplitude, the improvement wherein:
   said drive means includes analog means for developing an analog signal related in amplitude to the power required to maintain said amplitude constant,
   switching means responsive to the zero crossover times of said alternating displacement signal for selectively actuating said drive transducer with said analog signal to maintain said resonant frequency,
   said switching means including phase shift means for squaring said displacement signal,
   second integrator means for integrating said squared signal, and
   amplifier means responsive to said integrated squared signal for providing a timing signal phase shifted 90° from said zero crossover times to actuate said drive means in-phase with said mechanical system.

7. In a system for driving a dynamic mechanical system at its resonant frequency, said mechanical system having a displacement transducer for providing an alternating signal corresponding to the instantaneous displacement of said mechanical system, a drive transducer for imparting mechanical motion to said system, and drive means responsive to said displacement signal for actuating said drive transducer to maintain said mechanical system oscillating at said resonant frequency and at a constant amplitude, the improvement wherein:
   said drive means includes analog means for developing an analog signal related in amplitude to the power required to maintain said amplitude constant, switching means responsive to the zero crossover times of said alternating displacement signal for selectively actuating said drive transducer with said analog signal to maintain said resonant frequency, said switching means including peak detector means responsive to said displacement signal for generating a control level,
a source of a reference level, and
a gain control integrator means operating in response to said levels to adjust said analog signal in a sense to maintain a predetermined amplitude.

* * * * *